(12) United States Patent
Muenker et al.

(10) Patent No.: US 8,774,349 B2
(45) Date of Patent: Jul. 8, 2014

(54) DEVICE AND METHOD FOR NON-DESTRUCTIVELY TESTING CYLINDRICAL OR TUBE-SHAPED TEST OBJECTS BY MEANS OF X-RAYS

(75) Inventors: Martin Muenker, Gevelsberg (DE); Oliver Rokitta, Ennepetal (DE)

(73) Assignee: Yxlon International GmbH, Hamburg (DE)

( * ) Notice: Subject to any disclaimer, the term of this patent is extended or adjusted under 35 U.S.C. 154(b) by 347 days.

(21) Appl. No.: 13/142,442

(22) PCT Filed: Dec. 21, 2009

(86) PCT No.: PCT/EP2009/009187
§ 371 (c)(1),
(2), (4) Date: Jun. 28, 2011

(87) PCT Pub. No.: WO2010/075989
PCT Pub. Date: Jul. 8, 2010

(65) Prior Publication Data
US 2011/0274237 A1    Nov. 10, 2011

(30) Foreign Application Priority Data
Dec. 29, 2008  (DE) .................. 10 2008 063 193

(51) Int. Cl.
*A61B 6/03*     (2006.01)
*G01N 23/04*    (2006.01)

(52) U.S. Cl.
USPC ................................. 378/4; 378/21

(58) Field of Classification Search
USPC ................... 378/198, 197, 59, 57, 4
See application file for complete search history.

(56) References Cited

U.S. PATENT DOCUMENTS 4,350,942 A    9/1982  Heisner et al.
4,716,581 A    12/1987 Barud
(Continued)

FOREIGN PATENT DOCUMENTS

DE   19936408 A1   3/2001
EP    1985998 A1  10/2008
(Continued)

OTHER PUBLICATIONS

European Patent Office, International Search Report in International Patent Application No. PCT/EP2009/009187 (Mar. 31, 2010).

*Primary Examiner* — Irakli Kiknadze
(74) *Attorney, Agent, or Firm* — Leydig, Voit & Mayer, Ltd.

(57) ABSTRACT

A device for the non-destructive testing of cylindrical or tubular test objects using X-radiation in tomosynthesis or laminography includes a mounting device configured to be spatially fixed at a predetermined site, a carriage attached to the mounting device and movable on a guide device in a first direction parallel to an X-axis and a C-arm disposed on the carriage. An X-ray tube and a detector are disposed opposite one another on the C-arm. The X-ray tube is movable in a second direction that is perpendicular to the X-axis, perpendicular to a plane covered by the C-arm, and parallel to a Y-axis. The detector is movable in a third direction parallel to the second direction. The C-arm may alternatively be replaced by a half shell. Also a device for the non-destructive testing of cylindrical or tubular test objects using X-radiation in a CT process includes a mounting device configured to be spatially fixed at a predetermined site, a carriage attached to the mounting device and movable on a guide device in a first direction parallel to an X-axis and a C-arm disposed on the carriage rotatable about an axis of rotation that is parallel to a Y-axis. An X-ray tube and a detector are disposed opposite one another on the C-arm and spatially fixed with respect to one another. Also a method for the non-destructive testing of cylindrical or tubular test objects.

10 Claims, 2 Drawing Sheets

(56) References Cited

U.S. PATENT DOCUMENTS

| | | | |
|---|---|---|---|
| 5,014,293 A | | 5/1991 | Boyd et al. |
| 5,020,089 A | * | 5/1991 | Cramer et al. .................. 378/196 |
| 5,583,901 A | * | 12/1996 | Reitter et al. ...................... 378/4 |
| 6,374,937 B1 | * | 4/2002 | Galando et al. ................ 180/211 |
| 6,491,430 B1 | | 12/2002 | Seissler |
| 6,925,145 B2 | * | 8/2005 | Batzinger et al. ................. 378/59 |
| 7,016,457 B1 | | 3/2006 | Senzig et al. |
| 7,534,036 B2 | * | 5/2009 | Delmas et al. ................. 378/196 |
| 2001/0022834 A1 | * | 9/2001 | Graumann et al. ............ 378/198 |
| 2002/0003854 A1 | | 1/2002 | Ivan et al. |
| 2006/0078091 A1 | * | 4/2006 | Lasiuk et al. .................. 378/198 |
| 2008/0267345 A1 | | 10/2008 | Nagumo et al. |

FOREIGN PATENT DOCUMENTS

| | | |
|---|---|---|
| JP | 2005253788 A1 | 9/2005 |
| JP | 2006263052 A | 10/2006 |

\* cited by examiner

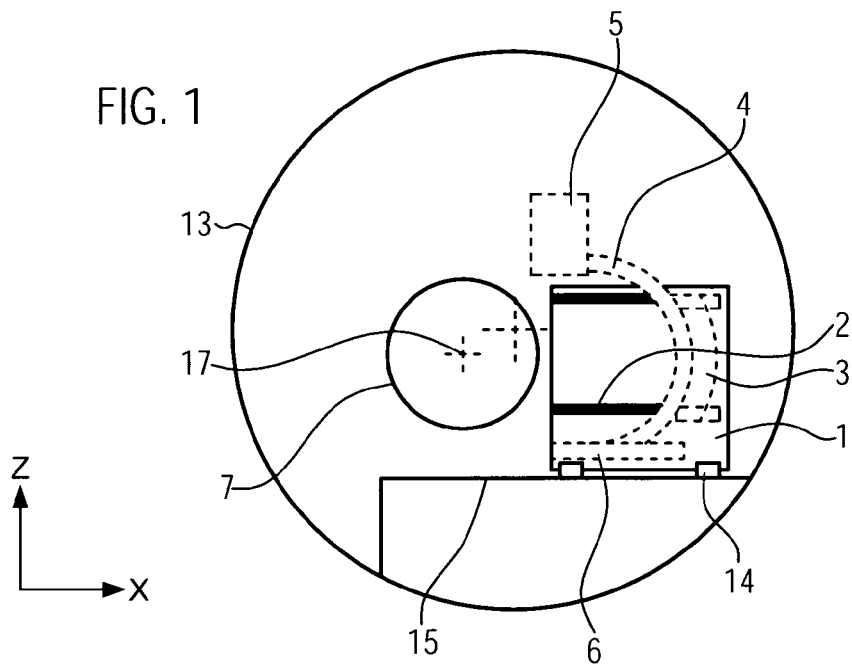
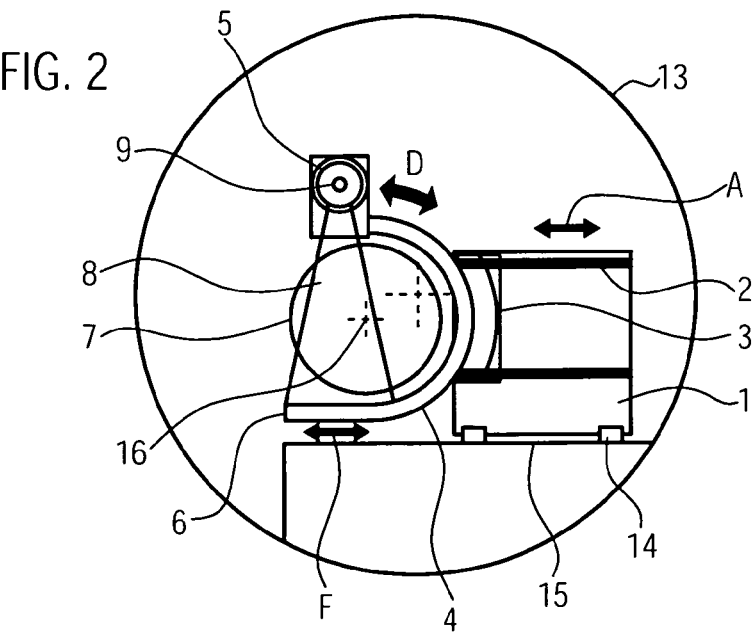

DEVICE AND METHOD FOR NON-DESTRUCTIVELY TESTING CYLINDRICAL OR TUBE-SHAPED TEST OBJECTS BY MEANS OF X-RAYS

CROSS REFERENCE TO RELATED APPLICATIONS

This application is a U.S. National Phase application under 35 U.S.C.§371 of International Application No. PCT/EP2009/009187, filed on Dec. 21, 2009, and claims benefit to German Patent Application No. DE 10 2008 063 193.0, filed on Dec. 29, 2008. The International Application was published in German on Jul. 8, 2010 as WO 2010/075989 A1 under PCT Article 21 (2).

FIELD

The invention relates to a device and a method for the non-destructive testing of cylindrical or tubular test objects by means of X-radiation by tomosynthesis, laminography or computed tomography.

BACKGROUND

Different methods are known for carrying out a non-destructive, volume testing of test items by means of X-radiation. These include for example tomosynthesis (TS), digital laminography (DL) or computed tomography (CT). These methods are familiar to a person skilled in the art so that it need not be explained in more detail here how these are carried out and on which physical foundations these are based.

When testing stationary, cylindrical or tubular test objects, problems frequently arise due to limited accessibility to the test object itself or to the test area at or inside the test object, e.g. because of limited overall space. Additionally, to obtain quantifiable, spatial information the test area must be mapped from several directions. Depending on the framework conditions and task set, accessibility in peripheral direction (in CT) or parallel to the cylinder axis (in TS and DL) may be available or necessary. Both mobile CT systems and systems with an open C-arm are known; this applies both to medical applications and also in non-destructive testing. However, such systems do not offer a sufficient variety of movement to achieve good test results with limited accessibility on the one hand, and on the other hand reflect the variety of limitations and demands.

SUMMARY

An aspect of the invention is to make available devices and methods with which a good, non-destructive testing is possible of stationary, cylindrical or tubular objects which allow only limited accessibility.

In an embodiment, the present invention provides a device for the non-destructive testing of cylindrical or tubular test objects using X-radiation in tomosynthesis or laminography including a mounting device configured to be spatially fixed at a predetermined site, a carriage attached to the mounting device and movable on a guide device in a first direction parallel to an X-axis and a C-arm disposed on the carriage. An X-ray tube and a detector are disposed opposite one another on the C-arm. The X-ray tube is movable in a second direction that is perpendicular to the X-axis, perpendicular to a plane covered by the C-arm, and parallel to a Y-axis. The detector is movable in a third direction parallel to the second direction. The C-arm may alternatively be replaced by a half shell.

In another embodiment, the present invention provides a device for the non-destructive testing of cylindrical or tubular test objects using X-radiation in a CT process including a mounting device configured to be spatially fixed at a predetermined site, a carriage attached to the mounting device and movable on a guide device in a first direction parallel to an X-axis and a C-arm disposed on the carriage rotatable about an axis of rotation that is parallel to a Y-axis. An X-ray tube and a detector are disposed opposite one another on the C-arm and spatially fixed with respect to one another.

In another embodiment, the present invention provides a method for the non-destructive testing of cylindrical or tubular test objects.

BRIEF DESCRIPTION OF THE DRAWINGS

Exemplary embodiments of the invention are described in more detail below with reference to the drawings, in which:

FIG. 1 shows a device according to an embodiment of the invention in a first position (travelling position), FIG. 2 shows the device from FIG. 1 in a second position in which a picture is taken (measuring position)

DETAILED DESCRIPTION

Figure 3:
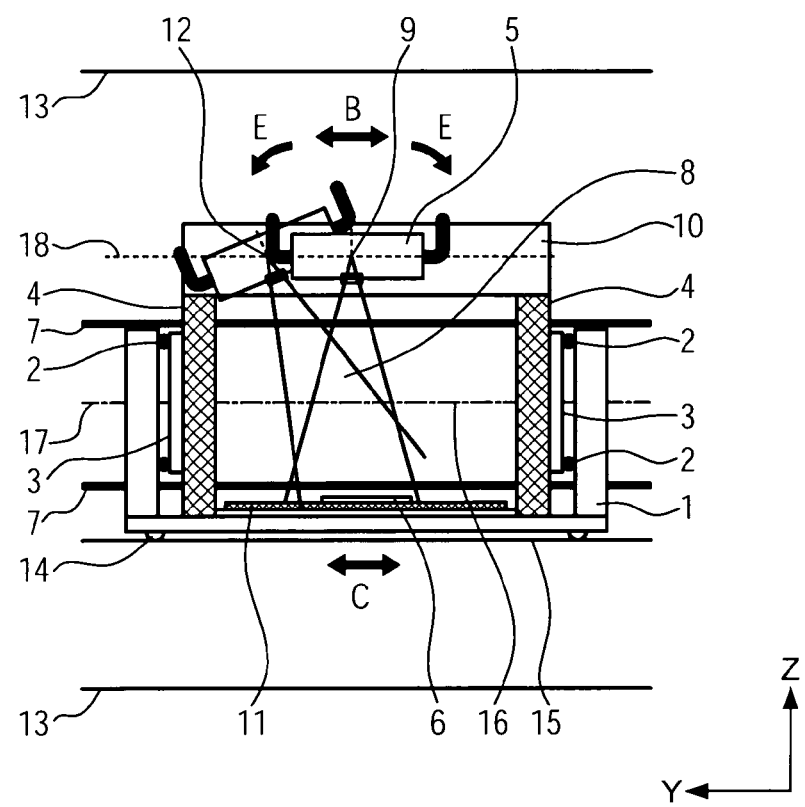
FIG. 3 shows the device according to FIG. 2 seen from the left.

In an embodiment, the present invention makes available a whole device which, in a tomosynthesis or laminography process, when there is limited accessibility can carry out the named method with a good result. The invention can, self-evidently, also be used with freely accessible or non-stationary test objects. According to an embodiment of the invention, four assemblies are combined with each other which cooperate to produce the above-named result. The mounting device is brought to the test site along the longitudinal direction of the tubular test object. By attaching to the mounting device a C-arm, extendable essentially perpendicular to the longitudinal axis of the tubular test object and attached to a carriage which is connected to the mounting device via the guide device, a positioning of the system of X-ray tube and detector located at the C-arm can be moved to the site located inside the "disk" which is defined by a cross-section of the tubular test object. Because the X-ray tube and the detector, which are arranged lying opposite each other on the C-arm, are moved in contrary directions parallel to each other, while fluoroscopic images are recorded, sequentially or continuously produced raw data in the form of projections are created. These raw images are evaluated interactively (multi-angle radiography) or provided for tomosynthesis or laminography. A volume image of the radiation-penetrated mapping area is calculated iteratively or by back-projection. On the basis of the above-described movement of the radiation source relative to the detector and the previous positioning of the C-arm as well as the mounting device, a test area inside the test object can be examined around a freely choosable fixed point.

An advantageous development of the invention provides that the C-arm can be rotated about an axis of rotation parallel to the Y-axis. It is thereby possible to rotate the C-arm with its attached components, X-ray tube and detector, about the longitudinal axis of the test object and then to fix it such that shaded structures with other penetration directions can be mapped. If for example one or more points are shaded in the vertical direction, the beam cone can be directed by a rotation about a suitable angle such that the shading is "bypassed", because it no longer lies in the beam cone which now comes from another direction.

A further advantageous development of the invention provides that the X-ray tube can be rotated about a tilt axis which runs parallel to the X-axis and passes through the focus of the X-ray tube. It is thus guaranteed, even when there are large relative shifts between X-ray tube and detector, that the detector itself is struck if the aperture angle of the beam cone is not too large. It is thus not necessary to use X-ray tubes with a very wide beam cone which generally have unfavourable mapping properties.

A further advantageous development of the invention provides that two C-arms arranged aligned in Y-direction and spaced apart from one another are present which are connected to one another, in the area of the X-ray tube via a top support to which the X-ray tube is attached and, in the area of the detector, via a bottom support to which the detector is attached. It is thereby guaranteed that a very precise guiding of both the detector and the X-ray tube at the C-arm can take place. This also applies to long movements of both components of the imaging system relative to one another.

A further advantageous development of the invention provides that each of the C-arms is connected to the mounting device allocated to each of these via its own carriage and a respective guide device allocated to the latter. A guiding of both C-arms that is stable, because it engages at both ends of the device, is thus achieved, with the result that no mechanical deformations, which could adversely affect the data recording and subsequent reconstruction, can occur.

A further advantageous development of the invention provides for a dimensionally stable half-shell instead of the combination of C-arms and supports. This then performs the tasks of the mentioned combination. This half-shell can perform a radiation-protection function in particular if the area adjoining the object is sealed off by flexible lead matting.

An embodiment of the invention provides a CT method, in which unlike in tomosynthesis or laminography, a relative movement between X-ray tube and detector is neither necessary nor desired. Instead, the raw data for recording an image of the test object are obtained by rotating the C-arm about an axis of rotation which is preferably, but not necessarily, approximately parallel to the longitudinal direction of the test object. A precise rotational movement necessary for the CT recording is guaranteed by the further structural configuration of the device.

A further advantageous development of the two devices according to the invention provides that the mounting device can be moved perpendicular to the X-axis. This means that when the test object is cylindrical it can be moved along its longitudinal axis. Thus any disk which corresponds to a cross-section of the test object can be approached by the mounting device and, because of the further device features—described above—any desired point of this disk examined.

Because radiation source and detector can be moved and positioned independently of one another, therefore also synchronously with one another, it is possible to approach any desired positions of a cylindrical test object within the test area along its longitudinal axis and there, because of the further device features—described above—examine any desired point of this disk without modifying the whole system.

A further advantageous development of the invention provides that the mounting device rests on tracks which run parallel to a tube to be examined, or is guided, actively or passively, by means of a track or a comparable device. A forced movement of the mounting device, which always takes place along the tubular test object, even if this were not cylindrical but bent, can thus be preset. In particular with an annular test object it is advantageous if the tracks run within a plane which lies parallel to the X-Y plane. The X-Y plane is defined by the plane in which the ring is located.

In another embodiment, the present invention provides a method in which the mounting device is positioned at the test site of the test object, thus the disk of the cross-section of the test object, and the mounting device is roughly aligned at the desired site and spatially fixed. An unintentional overall movement of the test device is thereby prevented. This can be positioned in different ways, for example by hand, by placing the device at the site in question, or by means of a motor which can also be remotely controlled. After the mounting device has been fixed, the carriage is extended along the selected disk of the test object, thus essentially perpendicular to the longitudinal axis of the test object, and the C-arm positioned such that the test site is covered by the beam cone. The carriage is then spatially fixed in this position. The raw data for an image are then recorded as described above for tomosynthesis or laminography, or according to the statements relating a CT method. After the raw data have been recorded, these can be evaluated interactively or provided to redesign the test item at the desired site by means of a suitable piece of software.

An advantageous development of the invention provides that the X-ray tube is rotated about the tilt axis during the recording, with the result that it always illuminates the whole of the detector. As already described above in connection with the device, it is thereby achieved that an X-ray tube with a narrower beam cone can be used but optimum raw data can still always be obtained for every direction of illumination.

A further advantageous development of the invention provides that, during tomosynthesis or laminography, after the spatial fixing of the carriage, the C-arm rotates about an axis of rotation parallel to the Y-axis until a suitable angle position is reached. This provides the possibility—as already stated above—of avoiding shading effects due to items which would shade the test area in one penetration direction, by choosing a different penetration direction where this shading object no longer lies in the beam cone.

A further advantageous development of the invention provides that, after recording the image, the carriage and then the mounting device are detached, the mounting device is then moved to the next test site and then the positioning of the mounting device resumes again, followed again by the steps according to the invention. This provides the possibility of successively examining several positions along the test object, wherein the new positioning can be achieved with various methods: for example by manually shifting the device or even—advantageously—using a motor which moves the mounting device. It has also already been indicated above that this can take place along tracks with the result that a forced guidance with optimum alignment of mounting device relative to test object is guaranteed.

A tunnel tube 13 in which a tubular test object 7 is located is shown in cross-section in FIG. 1—by way of example for a limited overall space. For reasons of simplicity it is assumed below, with regard to the description of the embodiment of FIGS. 1 to 3, that this is a rectilinear tubular test object 7, thus a cylindrical test object 7. A cartesian coordinate system is defined relative to this, the X-Z plane of which runs in the section plane represented in FIGS. 1 and 2. Thus the Y-axis stands perpendicular to the plane of drawing in FIGS. 1 and 2. The X-axis runs parallel to the horizontal and the Z-axis parallel to the vertical. In FIG. 3, on the other hand, a section through the tunnel tube 13 is shown which is perpendicular to the sections of FIGS. 1 and 2 and runs in the Y-Z plane. It is not essential to the understanding of the invention where the origin of the coordinates lies, as only movements along axes parallel to the X- or Y-axis or on rotations about axes which run parallel to the X- or Y-axis matter.

Underneath the test object 7 is a bearing surface 15 which runs in a horizontal plane, on which stands a device according to an embodiment of the invention. The device has a mounting device 1 which can be moved via rollers 14 on the bearing surface 15. Guide devices 2, for example tracks, are attached to the mounting device 1. These run parallel to the X-axis. However, they could also run at an angle to the X-axis; it is important only that they lie in the X-Z plane.

A carriage 3 which can be moved along the guide device 2 parallel to the X-axis is shown by a dotted line. A C-arm—likewise shown by a dotted line—is attached to the carriage 3. The C-arm 4 is thus also moved parallel to the X-axis if the carriage 3 is moved. The spatial arrangement of mounting device 1, guide device 2, carriage 3 and C-arm 4 can be better seen in the sectional representation of FIG. 3. Two C-arms 4 each are connected to the mounting device 1 via a carriage 3 along the guide device 2 in each case.

The imaging system is attached to the two free ends of the C-arm 4. In the embodiment, an X-ray tube 5 is attached to the top end and opposite this, at the bottom end, a detector 6. The detector 6 can also be moved parallel to the X-axis relative to the C-arm 4, in order that on the one hand it does not project beyond the whole width of the mappable area in the X-direction, and on the other hand in the shown situation of the device, as little as possible or not at all over the lateral dimensions of the mounting device 1. This is particularly advantageous when moving the mounting device 1 to a new test area of the test object 7.

In the situation shown in FIG. 1 the mounting device 1 is fixed in its spatial position, such that it is fixed relative to the disk which is represented by the cross-section of the test object 7 inside the X-Z plane. However, in the situation shown, after a detachment of the spatial fixing, the mounting device 1 can move to a different position parallel to the Y-axis and then be spatially fixed again, with the result that the disk there, which again runs parallel to the X-Z plane, can be examined. The displacement can take place via the rollers 14: for example by muscle power or by means of a motor which, for example. can be attached to the mounting device 1 and operated by remote control. It is not necessary to have to enter the tunnel tube 13, which facilitates the displacement of the mounting device 1 and can be advantageous in cases of potentially unfavourable environmental conditions (e.g. where there is a radiation load).

In order to be able to take a picture of the test object 7, the device is moved from its position shown in FIG. 1 into the position shown in FIG. 2. For this the carriage 3 is moved to the left in the first direction A which runs parallel to the X-axis. The detector 6 is also moved to the left in a fourth direction F which is parallel to the first direction A, with the result that it lies opposite the X-ray tube 5 and the beam cone 8 emerging from its focus 9. In this position the detector 6 is spatially fixed relative to the C-arm 4. The length of the movement in the first direction A of the C-arm 4 depends on which area of the test object 7 is to be examined. However, this is clear to a person skilled in the art, with the result that it need not be described in further detail.

Thereafter, in order to avoid any interfering effects which may be present, the C-arm 4 can rotate along the direction of rotation D about an axis of rotation 16. In the example shown the axis of rotation 16 coincides without this being limiting with the central axis 17 of the test object 7. Interference may result, for example, from the presence of a strongly absorbent structure inside the beam path, above or below the test area. By rotating the C-arm 4 about the direction of rotation D, the X-ray tube 5 and detector 6 move on an orbit and radiate at a different angle through the test object, with the result that the shading areas are no longer illuminated.

In FIG. 3 it is shown how the raw data for tomosynthesis or laminography are obtained; a CT process will also be explained below without being shown in the Figures.

FIG. 3 shows a further cross-section through the tunnel tube 13, wherein the direction of viewing is perpendicular to that of FIGS. 1 and 2, thus in X-direction. As already stated above with regard to FIG. 1, the device has two C-arms 4. The top ends of the C-arms 4 are connected to one another via a top support 10. The X-ray tube 5 is housed at this top support 10 such that it can be displaced in a second direction B along a line of movement 18 which runs parallel to the Y-axis.

A bottom support 11 lies opposite the top support 10, with the result that the bottom ends of the C-arms 4 can be connected to one another via same. The detector 6 is housed mobile at the bottom support 11 such that it can be moved along a third direction C which runs parallel to the second direction B and is thus also parallel to the Y-axis.

As the detector 6 and X-ray tube 5 move in opposite directions in laminography or tomosynthesis—as is familiar to a person skilled in the art and thus need not be explained in detail—the X-ray tube 5 can still also be tilted about a tilt axis 12 which passes through the focus 9. The tilt axis 12 is perpendicular to the plane of drawing and thus runs parallel to the X-axis. The X-ray tube 5 can thus be twisted clockwise about the tilt axis 12 along a direction of tilt E or against it vis-à-vis the neutral position which is shown on the right in FIG. 3. It is thus guaranteed that the beam cone 8 emerging from the focus 9 can be tracked such that it always illuminates the whole of the detector 6. If both components of the imaging system, X-ray tube 5 and detector 6, were moved to their extreme positions—thus for example the X-ray tube 5 all the way left and the detector 6 all the way right—, a very wide beam cone would otherwise have to be used in order to still illuminate the detector 6 at all. This is prevented by the possibility of turning the X-ray tube 5 in direction of rotation D.

When X-ray tube 5 and detector 6 are moving in contrary direction the raw data are obtained which are then processed by means of suitable software into a volume image of the radiation-penetrated mapping area for laminography or tomosynthesis. The laminography process is recursive and the tomosynthesis process iterative, without these needing to be explained in more detail as they are familiar to a person skilled in the art.

Nor will the wiring of the individual elements of the device be explained in more detail, as it is also known to a person skilled in the art how to wire these to one another.

If, instead of laminography or tomosynthesis, a CT process is carried out by means of the device according to an embodiment of the invention, the procedure is as follows: The C-arm 4 is rotated about an axis of rotation 16 which may, but does not have to, be the same as the axis of rotation given above in connection with the embodiment. The raw data are recorded, as in any known CT process, in a precise rotational movement. X-ray tube 5 and detector 6 are located in a fixed position opposite one another. The CT process is actually possible only due to the robust and precise guiding possibility of the C-arm 4 at the carriage 3.

It has already been explained above how the mounting device is moved from one measurement position to another. The C-arm 4 is again moved to the right (in FIG. 2) by means of the carriage 3 from the measurement position shown in FIGS. 2 and 3 with the result that it is again in the position shown in FIG. 1. At the same time the whole of the detector 6 is again also moved into the mounting device 1. The whole mounting device 1 is then moved parallel to the Y-axis.

Thus a forced movement of the mounting device 1 can be preset which is always along the tubular test object 7. In particular when there is an annular test object 7 (as described in the following paragraph) it is advantageous if the tracks run within a plane which lies parallel to the X-Y plane.

It is described below how the device according to an embodiment of the invention can be used to test a non-straight, cylindrical test object 7 bent in longitudinal direction, such as is the case for example with an annular tube of a particle accelerator. For this the mounting device 1 can for example be guided, actively or passively, on or along tracks or a comparable device which follow the curvature of the tube, with the result that the distance between mounting device 1 and test object 7 always remains the same. The mounting device 1 is then moved along the tracks as already stated above for the rectilinear movement in the case of a cylindrical test object 7. The mounting device 1 is then spatially fixed at the site where the disk to be examined is located—thus perpendicular to the longitudinal direction of the curved annular tube—and the C-arm 4 then extended by means of the carriage 3. The further steps are the same as those which are carried out when testing the cylindrical test object 7, as described above with regards to FIGS. 1 to 3.

In summary it can be said that, with the shown device according to the invention—this also applies to all further devices according to the invention which are not shown—as well as with the described method according to the invention, a non-destructive mapping of the inner structures can take place securely in stationary, tubular objects—be they cylindrical or bent in longitudinal direction—even where there are difficult boundary conditions. These boundary conditions include limited accessibility due to limited overall space, flexible usability with regard to a selective, extensive or volume examination, a projective and volume mapping, an interactive or also semi-automatic method as well as the possibility of remote control in view of protection from radiation. The invention can be adapted and scaled, without problems, as regards its size and radiation capacity, to the object-specific conditions. For example, it can be adapted along the object-specific preferred direction as predetermined in the embodiment shown in FIGS. 1 to 3 by the central axis 17 of the test object 7.

While the invention has been particularly shown and described with reference to preferred embodiments thereof, it will be understood by those skilled in the art that various changes in form and details may be made therein without departing from the spirit and scope of the invention.

LIST OF REFERENCE NUMBERS

1 Mounting device
2 Guide device
3 Carriage
4 C-arm
5 X-ray tube
6 Detector
7 Test object
8 Beam cone
9 Focus
10 Top support
11 Bottom support
12 Tilt axis
13 Tunnel tube
14 Roller
15 Bearing surface
16 Axis of rotation
17 Central axis
18 Line of movement
A First direction
B Second direction
C Third direction
D Direction of rotation
E Tilt direction
F Fourth direction

What is claimed is:

1. A device for the non-destructive testing of cylindrical or tubular test objects using X-radiation in tomosynthesis or laminography, the device comprising:
   a mounting device configured to be spatially fixed at a predetermined site;
   a carriage attached to the mounting device and movable on a guide device in a first direction parallel to an X-axis;
   a first C-arm disposed on the carriage;
   an X-ray tube and a detector disposed opposite one another on the first C-arm, the X-ray tube being movable in a second direction that is perpendicular to the X-axis, perpendicular to a plane covered by the first C-arm, and parallel to a Y-axis, and the detector being movable in a third direction parallel to the second direction; and
   a second C-arm aligned with the first C-arm in the Y-direction and spaced apart from the first C-arm, the first and second C-arms being connected by atop support in an area of the X-ray tube and a bottom support in an area of the detector, wherein the X-ray tube is attached to the top support and the detector is attached to the bottom support.

2. The device. recited in claim 1, wherein the first C arm is rotatable about an axis of rotation that is parallel to the Y-axis.

3. The device recited in claim 1, wherein the X-ray tube is rotatable about a tilt axis that is parallel to the X-axis and passes through a focus of the X-ray tube.

4. The device recited in claim 1, wherein the second C-arm is connected to the mounting device by another carriage and a respective other guide device associated therewith.

5. The device recited in claim 1, wherein the mounting device is movable in a direction perpendicular to the X-axis.

6. The device recited in claim 5, wherein the mounting device is one of disposed on tracks running parallel to a tube for examination, or guided, actively or passively, by a track.

7. The device recited in claim 1, wherein the X-ray tube and detector are independently movable, 8. A device for the non-destructive testing of cylindrical or tubular test objects using X-radiation in tomosynthesis or laminography, the device comprising:
   a mounting device configured to be spatially fixed at a predetermined site;
   a carriage attached to the mounting device and movable on a guide device in a first direction parallel to an X-axis;
   a first C-arm disposed on the carriage; and
   an X-ray tube and a detector disposed opposite one another on the first C-arm, the X-ray tube being movable in a second direction that is perpendicular to the X-axis, perpendicular to a plane covered by the first C-arm, and parallel to a Y-axis, and the detector being movable in a third direction parallel to the second direction,
   wherein the mounting device is movable in a direction perpendicular to the X-axis,
   wherein the mounting device is one of disposed on tracks running parallel to a tube for examination, or guided, actively or passively, by a track, and wherein the tracks are curved within a plane that is parallel to an X-Y plane.

9. A device for the non-destructive testing of cylindrical or tubular test objects using X-radiation in a CT process, the device comprising:
- a mounting device configured to be spatially fixed at a predetermined site;
- a carriage attached to the mounting device and movable on a guide device in a first direction parallel to an X-axis;
- a first C-arm disposed on the carriage, the first arm being rotatable about an axis of rotation that is parallel to a Y-axis; and
- an X-ray tube and a detector disposed opposite one another on the first C-arm and spatially fixed with respect to one another,
- wherein the mounting device is movable in a direction perpendicular to the X-axis
- wherein the mounting device is one of disposed on tracks running parallel to a tube for examination, or guided, actively or passively, by a track, and
- wherein the tracks are curved within a plane that is parallel to an X-Y plane.

10. The device recited in claim 9, wherein the X-ray tube and detector are independently movable.

* * * * *